(12) United States Patent
Daly

(10) Patent No.: US 9,481,634 B2
(45) Date of Patent: Nov. 1, 2016

(54) AMINE MINING COLLECTORS

(71) Applicant: Thomas P. Daly, Arlington Heights, IL (US)

(72) Inventor: Thomas P. Daly, Arlington Heights, IL (US)

(*) Notice: Subject to any disclaimer, the term of this patent is extended or adjusted under 35 U.S.C. 154(b) by 0 days.

(21) Appl. No.: 15/005,162

(22) Filed: Jan. 25, 2016

(65) Prior Publication Data

US 2016/0214933 A1    Jul. 28, 2016

Related U.S. Application Data

(60) Provisional application No. 62/107,857, filed on Jan. 26, 2015, provisional application No. 62/247,029, filed on Oct. 27, 2015.

(51) Int. Cl.
| | | |
|---|---|---|
| *C07C 329/14* | (2006.01) | |
| *C07C 217/08* | (2006.01) | |
| *C11D 1/42*   | (2006.01) | |
| *B03D 1/00*   | (2006.01) | |

(52) U.S. Cl.
CPC .............. *C07C 217/08* (2013.01); *B03D 1/00* (2013.01); *C07C 329/14* (2013.01); *C11D 1/42* (2013.01)

(58) Field of Classification Search
CPC .................................................... C07C 217/08
See application file for complete search history.

(56) References Cited

U.S. PATENT DOCUMENTS

| | | | | |
|---|---|---|---|---|
| 3,135,805 A * | 6/1964 | Gilmont | .................... | C08F 4/32 260/DIG. 28 |
| 4,186,254 A * | 1/1980 | Cuscurida | .......... | C08G 18/1833 521/115 |
| 6,458,999 B1 * | 10/2002 | Daly | .................... | C07C 217/08 564/348 |
| 9,090,638 B2 * | 7/2015 | Daly | .................... | C07C 309/14 |
| 2015/0329486 A1 * | 11/2015 | Daly | .................... | C07D 401/04 560/1 |
| 2016/0052868 A1 * | 2/2016 | Daly | .................... | C07C 205/15 560/129 |
| 2016/0194283 A1 * | 7/2016 | Daly | .................... | C07D 213/74 546/312 |

FOREIGN PATENT DOCUMENTS

DE           1 163 850 B1 *  2/1964

OTHER PUBLICATIONS

Lai et al. Polymer Chemistry (2014), 5, 1650.*
Xu, et al. Huanjing Huaxue (1988), 7(1), 69-80.*
Xu, et al. Huanjing Kexue Xuebao 6(4), pp. 489-507 (1986).*

* cited by examiner

*Primary Examiner* — Nyeemah A Grazier
(74) *Attorney, Agent, or Firm* — Clifford H. Kraft

(57) ABSTRACT

A family of amine mining collectors that uses alkoxylates allows for the easy adjustment of solubility and molecular weight useful because anionic and cationic mineral collectors require such varying degrees of solubility and molecular weight. The family of the present invention allows for the optimization of both parameters and an increase in collector efficiency.

12 Claims, 6 Drawing Sheets

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R$^1$ is chosen from -H, -OH, -CH$_3$, -CH$_2$CH$_3$. n and m are an integers greater than zero.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R1 is chosen from -H, -OH, -CH$_3$, -CH$_2$CH$_3$. n and m are an integers greater than zero.

Figure 3

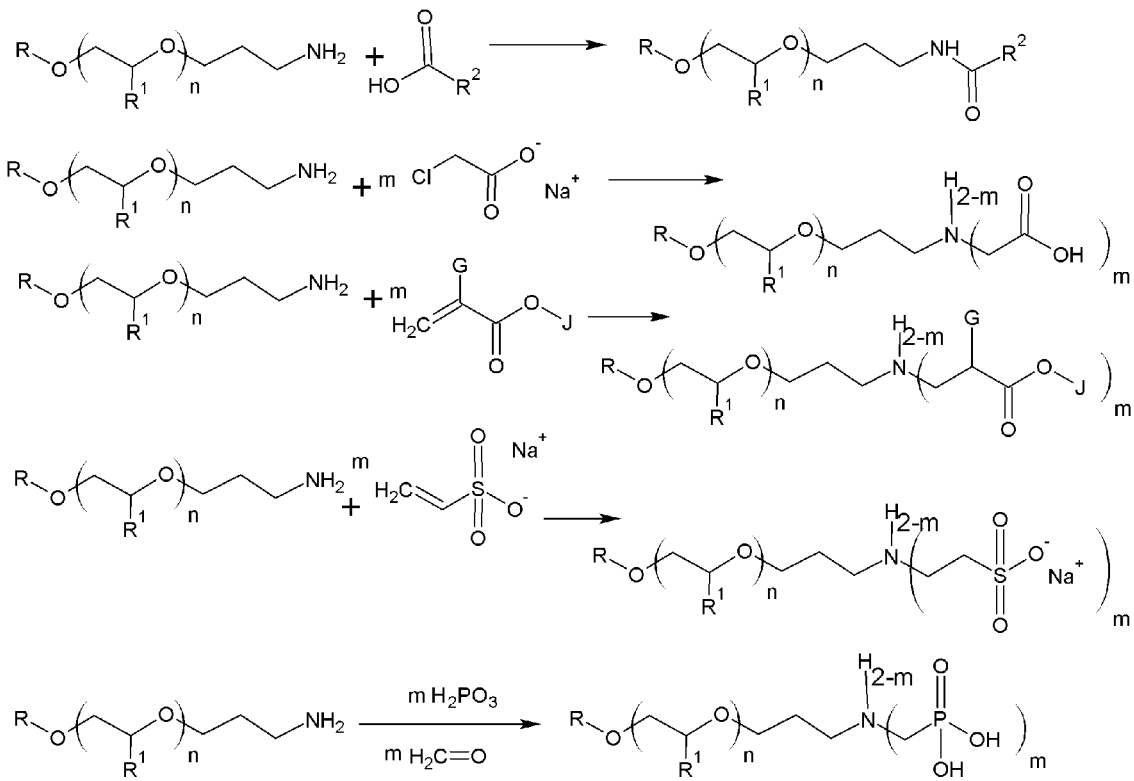

R and R2 are independantly chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R1 is chosen from -H, -OH, -CH$_3$, -CH$_2$CH$_3$. n is an integer greater than zero, m is 1 or 2, G is chosen from -H, -OH, -CH2, -CH3, J is chosen from -H, linear or branched, saturated or unsaturated, cyclic or acyclic from 1 to 22 carbons, -(CH2CH2O)xH, -(CH2CH(CH3)O)yH, -(CH2CH(CH2CH3)O)zH, -(CH2CH2O)x-(CH2CH(CH3)O)y-(CH2CH(CH2CH3)O)zH. x,y, and z are integers 0 or greater.

R is chosen from $-Si(CH_3)_3$, $-Si(CH_2)_mH$, $-Si(CH_2)_mCH_3$, $-H$, linear or branched, saturated or unsaturated, cyclic or acyclic from 1 to 22 carbons, $R^1$ is chosen from $-H$, $-OH$, $-CH_3$, $-CH_2CH_3$. n and m are an integers greater than zero.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R$^1$ is chosen from -H, -OH, -CH$_3$, -CH$_2$CH$_3$. n and m are an integers greater than zero.

R is chosen from -Si(CH$_3$)$_3$, -Si(CH$_2$)$_m$H, -Si(CH$_2$)$_m$CH$_3$, -H, linear or branched, saturated or unsaturated, cyclic or acyclic from 1 to 22 carbons, R$^1$ is chosen from -H, -OH, -CH$_3$, -CH$_2$CH$_3$. n and m are an integers greater than zero.

AMINE MINING COLLECTORS

This application is related to, and claims priority from, U.S. Provisional Patent applications No. 62/107,857 filed Jan. 26, 2015 and 62/247,029 filed Oct. 27, 2015. Applications 62/107,857 and 62/247,029 are hereby incorporated by reference in their entireties.

BACKGROUND

1. Field of the Invention

The present invention relates to the field of amine mining collectors and more particularly to a class of ether amines.

2. Description of the Problem Solved by the Invention

Many commercially important mineral ores are mined from the earth in relatively low concentration. For instance, in Minnesota's Mesabi range, the ore consists of approximately 25% iron. Prior to further processing, the desired minerals must be concentrated. The present invention improves the process of concentrating the desired mineral.

SUMMARY OF THE INVENTION

The present invention relates to the field of amine mining collectors that improve the yield of ore concentration. The use of amines with sufficient water solubility, that form strong water insoluble complexes with the desired mineral, and not with competing minerals results in a higher yield of the desired minerals. The family of amine, xanthate and dithiocarbamate collectors of the present invention does just that.

DESCRIPTION OF THE FIGURES

Attention is now directed to the following figures that describe embodiments of the present invention:

FIG. 3 shows the synthesis of derivatives of the cationic collectors.

DETAILED DESCRIPTION OF THE INVENTION

Mineral ores that are concentrated by floatation are dug out of the ground and ground to a predefined small particle size. The grains or ore are then treated with various surface active molecules and pumped into a floatation pond where dissolved air is introduced. The ore binds to the collector, that creates a water insoluble particle. This water insoluble complex is then floated to the surface by exclusion from the water into the air bubbles that form in dissolved air floatation. Frothers keep a thick head of foam that supports the mineral at the surface until rakes of booms can skim the mineral complex into hoppers for further processing. Ideally, the non target components of the dirt/ore mixture are left to settle to the bottom of the floatation ponds, thus concentrating the desired minerals to an extent that they can then enter the next processing steps, be it reduction, purification or other processing steps.

The present invention utilizes alkoxylates as the backbone of the collector. By varying the side chains on the collector and the chain length, either though increasing the number of repeating units, or by utilizing different chain length or conformations of alcohols to initiate the alkoxylation adjustments to the water solubility, frothing potential and density of the mineral-collector complex can be made. These adjustments allow for the optimization of the collector, by increasing the yield of the target mineral and reducing the collection of non-target minerals, such as silicates.

Figure 1:
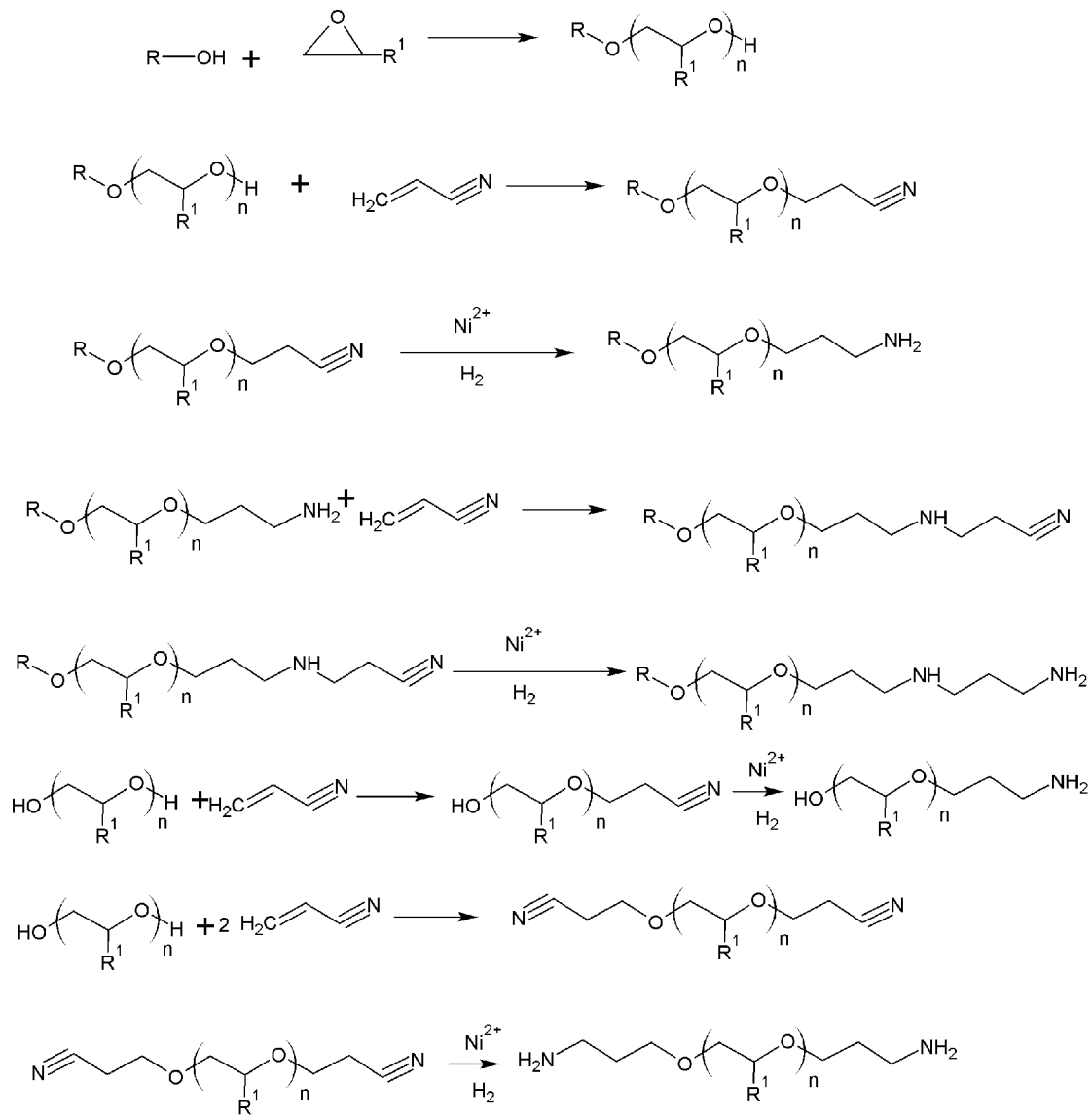
FIG. 1 shows the synthesis of novel ether amine cationic mineral collectors.

FIG. 1 shows the synthesis of primary amine and diamine collectors. Water is typical used to make polyalkoxylates. The resulting polyalkoxylates have 2 terminal hydroxyls and can react with 2 moles of acrylonitrile to form the di-primary amine. The use of diols and polyols, such as resorcinol, glycerin, neopentyl glycol, and pentaerythritol produce multiple hydroxyls and the analogous products can be formed. The higher polyols beyond diols, introduce branching, which is useful for lower pour points and easier handling, particularly in cold climates. While the figure shows the alkyl portion, R being from 1 to 8 carbons, this is the preferred range for the ore that is mined today. Higher carbon chains show promise in more unusual ores where heavier species are being floated. The invention covers these higher carbon chain analogs as well. This analog holds true for all subsequent figures as well.

The use of a monohydric alcohol, such as methanol, ethanol, propanol or butanol results in a polyalkoxylate with just one terminal hydroxyl to react the acrylonitrile with, resulting in a primary amine collector. Utilizing higher carbon number alcohols reduces the water solubility of both the collector and the collector-mineral complex. Non-linear alcohols, like phenol, cylcohexanol, isopropanol, or t-butanol reduces the pour point for easier handling in cold climates.

A diamine can also be formed by reacting the previously formed primary amine with an additional mole of acrylonitrile, which is then reduced to form the diamine. This same addition can be done with the primary diamines to yield di-(diamines). The Michael Addition of acrylonitrile to the alcohol and the amine is well known, as is the reduction of the nitrile to the amine with sponge nickel or other sponge metals, either promoted or not, with hydrogen. The reduction typically takes place at a pressure between 400 to 800 psi at less than 40 C over 4 to 12 hours. The Michael Addition is typically done by adding acrylonitrile to the alcohol or amine at ambient temperature with cooling at such a rate as to maintain temperature. Elevated temperatures lead to polymerization of the acrylonitrile. If needed, a catalytic amount of caustic may be used to accelerate the Michael Addition with alcohols. The yields are typically in excess of 96% and no further purification is necessary for a commercial product. These collectors are useful where cationic collectors are required, such as iron ore and potash.

Figure 2:
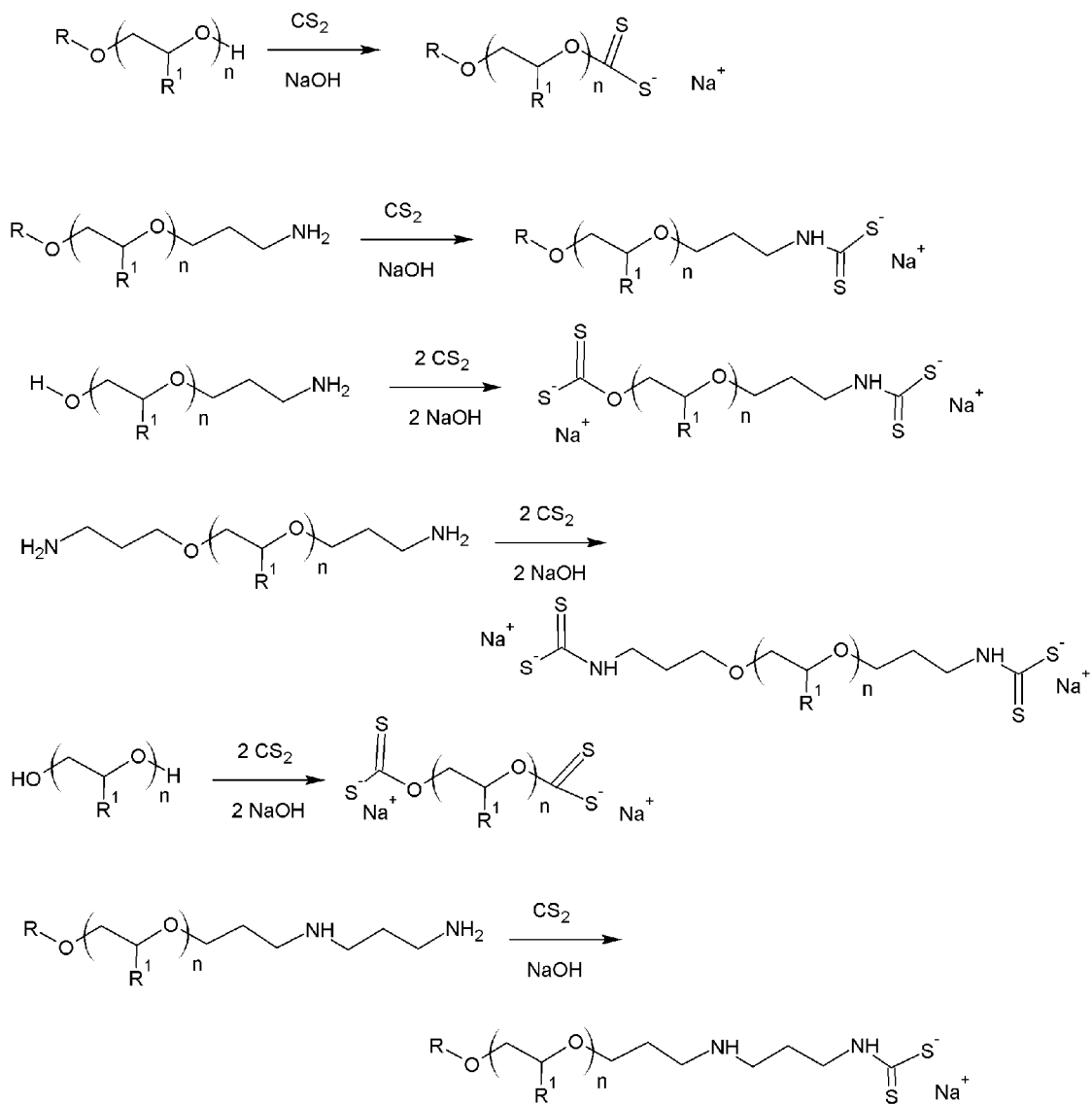
FIG. 2 shows the synthesis of novel anionic mineral collectors.

FIG. 2 shows the synthesis of the anionic analogs of the collectors in FIG. 1. The xanthates and dithiocarbamates. The di-dithiocarbamates may be made from the diamines. The anionic collectors are typically used in sulfide ores. The same solubility trends apply to the anionics as to the cationic collectors of FIG. 1. The xanthates are synthesized by reacting carbon disulfide ($CS_2$) with the alcohol group under basic conditions. The dithiocarbamates are made similarly, but reacting an amino group instead of an alcohol group. The result is a salt of the xanthate or dithiocarbamate. The salt shown in FIG. 2 is always a sodium salt, but any cationic salt is possible and part of the invention. The xanthates and dithiocarbamates can be made as the salts of amines, as well as of mineral bases.

Figure 4:
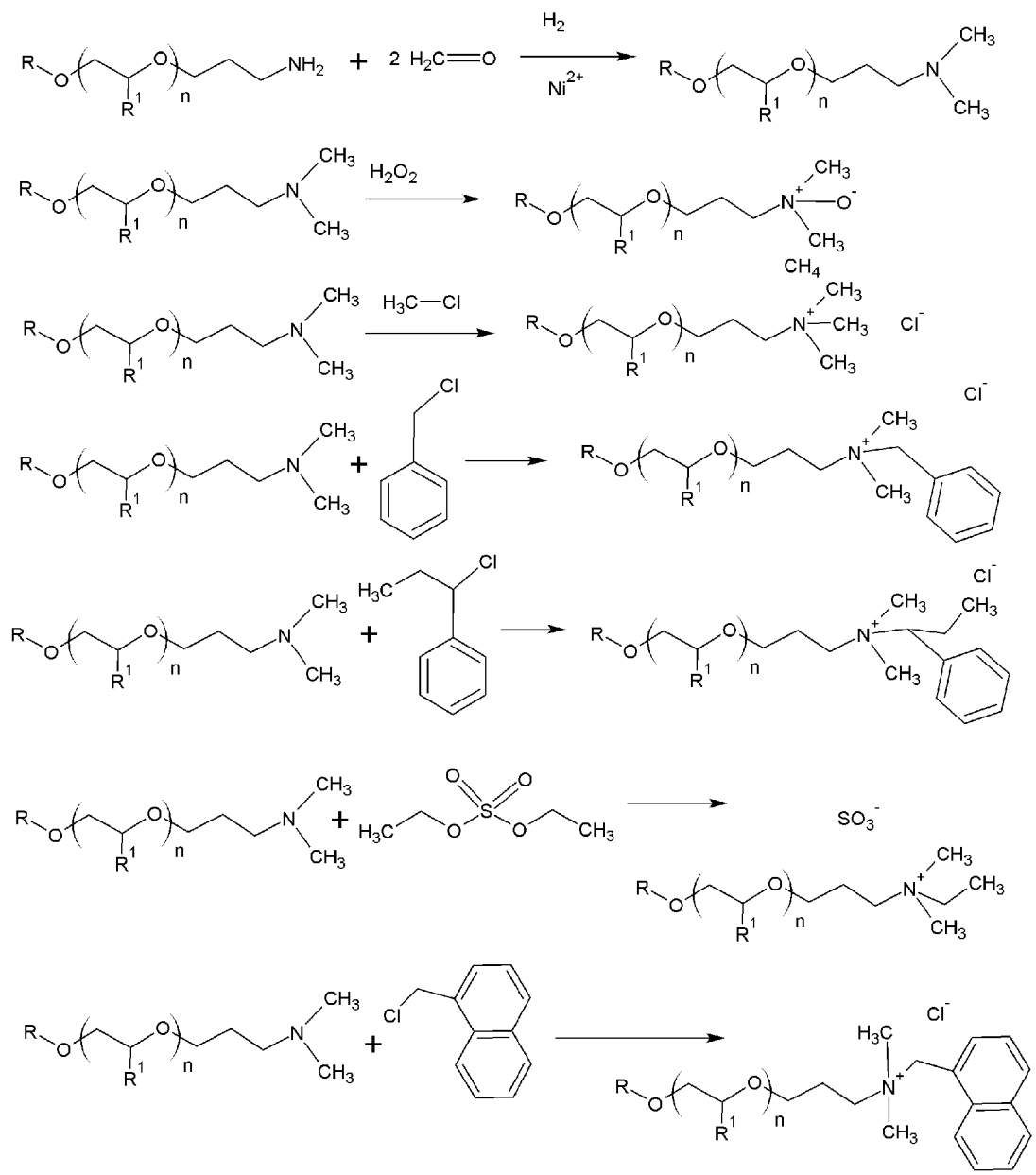
FIG. 4 shows the synthesis of tertiary amine derivatives.

The collectors of the present invention have additional uses as well. The cationic collectors have utility in personal care as surfactants, cleaners, emollients, rheology modifiers, and to buffer the products. The primary amines and diamines also have utility in asphalt as antistrips. FIG. 3 shows several derivatives. Amides with fatty acids of the cationic collectors are made simply by combining the cationic collector with the desired fatty acid, typically stearic acid or coconut fatty acid and heating to remove a mole of water for each amide group formed. The amides are versatile rheology modifiers. Amphoterics of the cationic collectors can be made through the reaction of sodium monochloroacetic acid (reflux 1:1 molar equivalents of SMCA for approximately 8 hours), or for a salt free form, acrylic acid or methacrylic acid may be reacted by adding the acid at ambient temperature or below to the cationic collector with sufficient cooling to keep the temperature below 30 C. The esters can be made by reacting the esters of the acids. A diaddition can be made to the amino group by continuing the reactions. Sulfonates can be made by reacting sodium vinyl sulfonate, propane sultone or butane sultone, or higher sultones can be reacted similarly to create the sulfonates with a longer carbon chain between the nitrogen and the sulfur. Phosphonates can be made by reacting phosphonic acid and formaldehyde. The salted products derivatives of the cationic collectors in FIG. 3 can be in their free form through ion exchange or be salted with any other cation. FIG. 4 shows that tertiary amines can be made by reacting 2 moles of formaldehyde, followed by a reduction with sponge nickel under similar conditions to the nitrile reductions in FIG. 1. The tertiary amines can then be made into quaternaries or amine oxides. The quaternaries of methyl chloride, diethylsulfate, ethyl benzyl chloride, and benzyl chloride are all facile reactions at ambient temperature that yield the analogous quaternaries.

Figure 5:
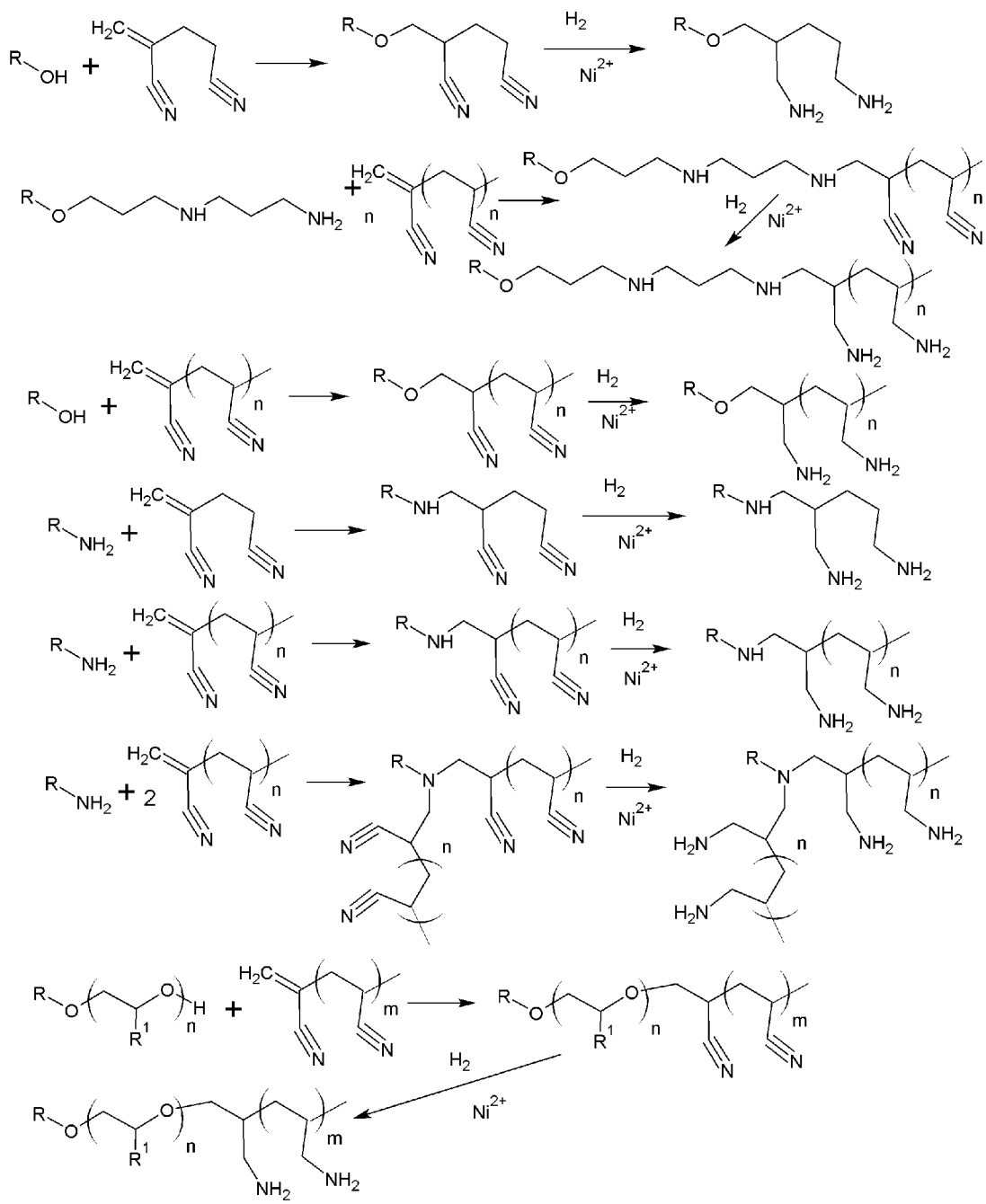
FIG. 5 shows the synthesis of polyprimary amines.

FIG. 5 shows the synthesis of novel collectors based on allylic polynitriles that are then reduced to the polyamines. This unique approach allows for the synthesis of polyprimary amines. The starting material may be an alcohol, an amine, a polyamine such as Tallow Diamine, common trade name Akzo Duomeen T, or polyether amine, such as Air Products DA-14, ethoxylated amines, such as Akzo Ethomeet T12, or ethoxylated ether amines, such as Air Products E-17-5. In the case of primary amines, a second equivalent of the allylic polyacrylonitrile can be added, versus the secondary amines that can only accept one equivalent. Any alcohol or amine functional starting material may be reacted with the allylic polyacrylonitrile and then reduced to form the polyamine is part of this invention.

Figure 6:
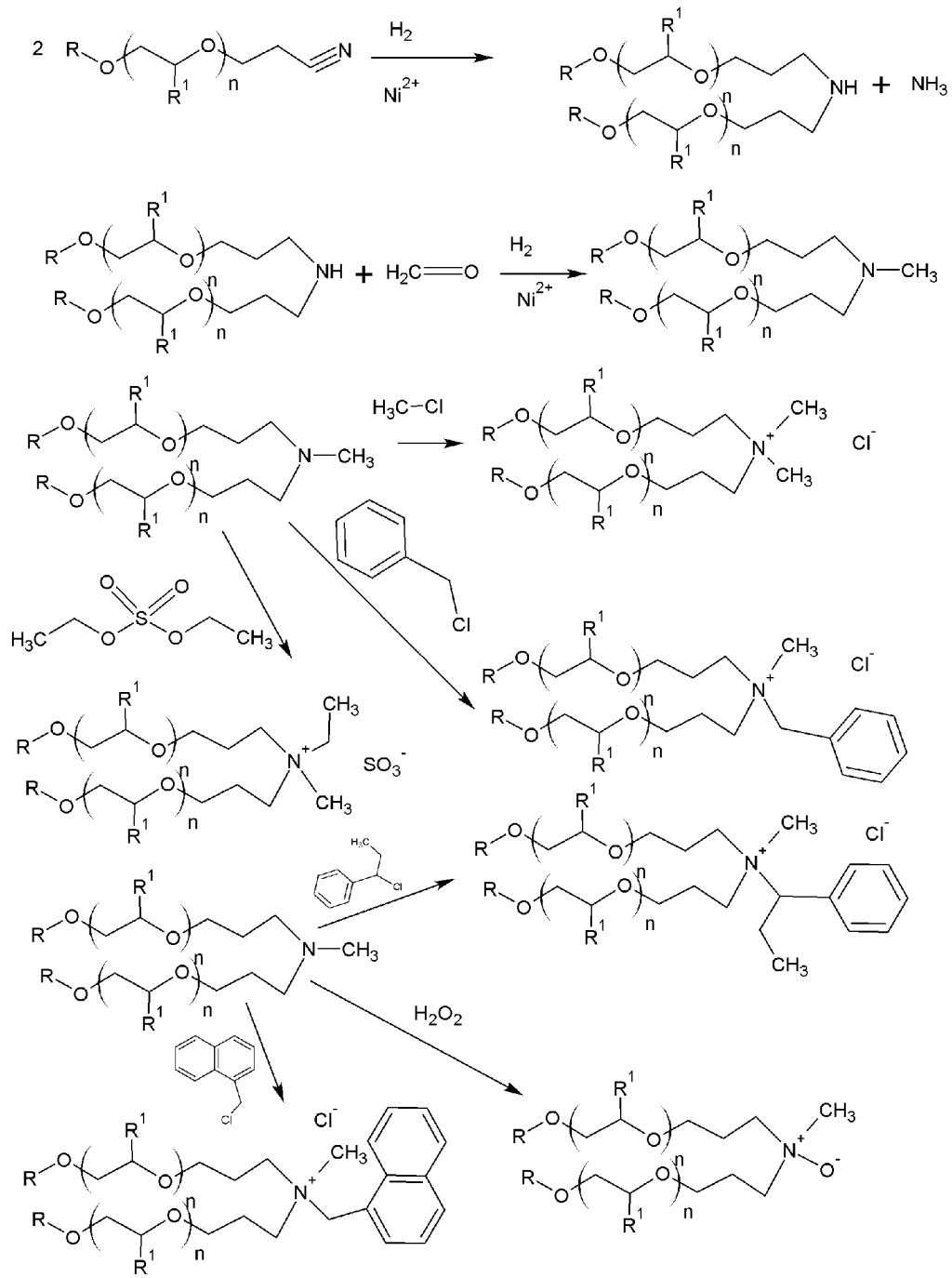
FIG. 6 shows the synthesis of secondary amines and derivatives.

FIG. 6 shows the synthesis of the secondary amines. In FIG. 6, the reactants are 2 moles of the same ether nitrile, but this need not be the case. R and $R^1$ may be different and even a wade range of blends may be used which will give a mixture of symmetric and asymmetric secondary amines. The ether nitriles of the invention may also be reacted alkyl nitriles, such as tallow nitrile, or more conventional ether nitriles, such as the ether nitrile formed by the synthesis of fatty alcohols such as Exxal 10 and acrylonitrile to form asymmetric secondary amines and even the nitriles formed from acrylonitrile and hydroxyl terminated siloxanes or silyl alcohols. The use of differing nitriles allows the chemist to produce secondary amines with a range of hydrophobicities and surfactancies. Conditions for the synthesis are more severe than the synthesis of the primary amines. The reaction generally takes 2 hrs at 220 C, but only about 300 psi pressure of hydrogen. Typical sponge nickel may be used, but beta branched products to appear in larger quantities. A nickel carbonate catalyst will reduce this byproduct formation. While FIG. 6 only shows the synthesis of symmetric secondary amines, the asymmetric secondary amines and their derivatives are part of this invention. The dimethyl quaternary shown in row 3 of FIG. 6 is particularly well suited to treated drilling clays to form hydrophobic clays for use in oilfield drilling muds, as well as biodegradeable fabric softeners. These dimethyl quats me be formed as either the sulfate or chloride salt depending on the methylating agent, typically DMS or methyl chloride. The bezyl chloride quats are useful for antimicrobials and corrosion inhibitors. The ethylbenzyl and naphtha quats are anti-fungal as well.

The symmetric tertiary amine of the first row of FIG. 6 is obtained with slightly different conditions. An 85% yield of tertiary amine is obtainable by running the reaction at a lower pressure, ~100 psi, for 4-6 hrs. The corresponding asymmetric tertiary amines can be made by varying the nitriles used as starting materials in the reaction vessel. Similarly, the derivatives, such as amine oxides, and quaternaries analogous to the those shown with the methyl tertiary amine are similarly obtained. The tertiary polyalkoxylate quaternaries are particularly useful as hair conditioners, particularly when a silyl nitrile is used as a starting material.

Similar to FIGS. 2, 3, and 4, the amines in FIG. 5 and FIG. 6 can be derivatized into tertiary amines, amine oxides, quaternaries, sulfonates, sulfates, betaines, betaine esters, phosphonates and alkoxylates. The amine products taught in this invention are used in mineral floatation, either alone or in combination with other known collectors, and or with non-ionic surfactants or other frothing aids, asphalt emulsifiers.

Several descriptions and illustrations have been presented to enhance understanding of the present invention. One skilled in the art will know that numerous changes and variations are possible without departing from the spirit of the invention. Each of these changes and variations are within the scope of the present invention.

I claim:

1. The mining collector of the following structure:

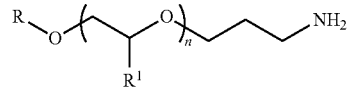

R is linear or branched, saturated or unsaturated, cyclic or acyclic alkyl group from 1 to 9 carbons, $R^1$ is chosen from —$CH_3$, or —$CH_2CH_3$; n is an integer greater than one.

2. The mining collector of claim 1 wherein R=—$C(CH_3)_3$, $R^1$=—CH3 and n=3.

3. The amine collector of claim 1 wherein R=—CH$(CH2)_2$, $R^1$=—$CH_3$, and n=3.

4. The amine collector of claim 1 wherein R=—$CH_3$, $R^1$=—$CH_2CH_3$, and n=3.

5. The mining collector of the following structure:

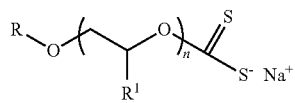

R is linear or branched, saturated or unsaturated, cyclic or acyclic alkyl group from 1 to 8 carbons, $R^1$ is chosen from —H, —$CH_3$, or —$CH_2CH_3$; n is an integer greater than zero.

6. The mining collector of claim 5 wherein R=—$C(CH_3)_3$, $R^1$=—CH3 and n=3.

7. The amine collector of claim 5 wherein R=—CH$(CH2)_2$, $R^1$=—$CH_3$, and n=3.

8. The amine collector of claim 5 wherein R=—$CH_3$, $R^1$=—$CH_3$, and n=3.

9. The surfactant of the following structure:

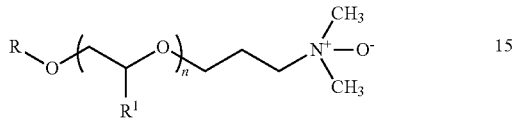

Where R is linear or branched, saturated or unsaturated, cyclic or acyclic alkyl group from 1 to 8 carbons, $R^1$ is chosen from —$CH_3$, or —$CH_2CH_3$; n is an integer greater than zero.

10. The surfactant of claim 9 wherein =—$C(CH_3)_3$, $R^1$=—CH3 and n=3.

11. The amine collector of claim 9 wherein R=—CH$(CH2)_2$, $R^1$=—$CH_3$, and n=3.

12. The amine collector of claim 9 wherein R=—$CH_3$, $R^1$=—$CH_3$, and n=3.

* * * * *